United States Patent [19]
Scott

[11] Patent Number: 6,155,993
[45] Date of Patent: Dec. 5, 2000

[54] KINESIOLOGICAL INSTRUMENT FOR LIMB MOVEMENTS

[75] Inventor: Stephen H. Scott, Kingston, Canada

[73] Assignee: Queen's University at Kingston, Kingston, Canada

[21] Appl. No.: 09/281,915

[22] Filed: Mar. 31, 1999

[51] Int. Cl.[7] ........................................................ A61B 5/00
[52] U.S. Cl. ................................................................. 600/595
[58] Field of Search ..................................... 600/587, 595; 73/379.01, 379.02, 379.03

[56] References Cited

U.S. PATENT DOCUMENTS

| | | |
|---|---|---|
| 4,830,021 | 5/1989 | Thornton ................................. 600/595 |
| 4,878,663 | 11/1989 | Luquette . |
| 4,934,694 | 6/1990 | McIntosh . |
| 5,201,772 | 4/1993 | Maxwell . |
| 5,231,998 | 8/1993 | Rosen et al . |
| 5,466,213 | 11/1995 | Hogan et al. . |
| 5,476,441 | 12/1995 | Durfee et al. . |
| 5,620,410 | 4/1997 | Kaiser et al. . |
| 5,830,160 | 11/1998 | Reinkensmeyer . |
| 5,865,714 | 2/1999 | Marlowe . |

OTHER PUBLICATIONS

Centre for Rehabilitation and Engineering Studies (CREST), University of Newcastle upon Tyne, "Motorized Upper Limb Orthotic Systems (MULOS)" Apr. (1998). (Document downloaded from website).

Georgopoulos, A.P., et al., "On the relations between the direction of two–dimensional arm movements and cell discharge in primate motor cortex." *J. Neurosci.* 2:1527–37 (1982).

Gomi, H., et al., "Equilibrium–point control hypothesis examined by measured arm stiffness during multijoint movement." *Science* 272:117–20 (1996).

Goodbody, S.J., et al., "Temporal and amplitude generalization in motor learning. " *J. Neurophysiol.* 79:1825–38 (1998).

Kalaska, J.F., et al., "A comparison of movement direction–related versus load direction–related activity in primate motor cortex, using a two–dimensional reaching task." *J. Neurosci.* 9:2080–102 (1989).

Shadmehr, R., et al., "Adaptive representation of dynamics during learning of a motor task." *J. Neurosci.* 14:3208–24 (1994).

Sainburg, R.L., et al., "Control of limb dynamics in normal subjects and patients without proprioception." *J. Neurophysiol.* 73:820–35 (1995).

Turner, R.S., et al., "Directional variation of spatial and temporal characteristics of limb movements made by monkeys in a two–dimensional work space." *J. Neurophysiol.* 74:684–97 (1995).

*Primary Examiner*—Max Hindenburg
*Attorney, Agent, or Firm*—Stephen J. Scribner; Carol Miernicki Steeg

[57] ABSTRACT

An instrument for measuring kinetic and kinematic variables of multijoint motor tasks comprises a linkage having four links connected at four joints, each joint having articulation about an axis, the four axes of articulation being substantially parallel, limb coupling means for coupling a limb to the linkage, the limb coupling means maintaining alignment of centers of rotation of two joints of the limb with centers of rotation of two joints of the linkage, means for providing a load to at least one of the two joints of the linkage, means for obtaining data respecting angular position of at least one of the joints of the linkage. In an alternative embodiment, the linkage has only two links. The invention also provides methods for detecting, monitoring, and/or treating neural and/or muscular problems associated with impaired movement of limbs.

40 Claims, 11 Drawing Sheets

C

D

KINESIOLOGICAL INSTRUMENT FOR LIMB MOVEMENTS

FIELD OF THE INVENTION

This invention relates to an instrument for detecting, quantifying, and treating neural and/or muscular problems associated with impaired movement of the limbs, and for investigating how sensory information is converted into coordinated motor behavior in the central nervous system (CNS).

BACKGROUND OF THE INVENTION

Investigations of neural and/or muscular problems associated with impaired movement of the limbs, and of how coordinated motor behavior is planned and controlled by the central nervous system (CNS), ideally require the ability to monitor the movement of one or more joints of a limb under various mechanical conditions. A number of devices have been proposed for manipulating limbs under various conditions of load, but most of such devices are concerned with end-point loading of the limb. For example, U.S. Pat. No. 5,210,772, issued Apr. 13, 1993 to Maxwell, relates to a complex linkage which attaches to a subject's limb at a single point, and provides forces to resist limb movement. U.S. Pat. No. 5,466,213, issued Nov. 14, 1995 to Hogan et al. describes a robotic therapist consisting of a computer-controlled mechanical linkage that interfaces with a subject's hand and guides the arm through a range of movement. U.S. Pat. No. 5,830,160, issued Nov. 3, 1998 to Reinkensmeyer relates to a system consisting of a guide that permits limb movement along a linear path. Forces can be applied to resist or aid movement of the limb along the path. While these systems may be useful in a rehabilitation program for individuals with impaired movement of limbs, they are not readily able to provide information related to the mechanics of limb movement.

When an individual suffers brain injury from stroke, trauma, or the like, there often results decreased control of one or more limbs. This decreased control is associated with a partial loss of the central nervous system's ability to coordinate motor patterns of muscles at various joints of the limb to smoothly move the limb in space. Effective treatment of such disabilities can be enhanced with detailed knowledge of the mechanics of limb movements; however, none of the instruments proposed to date are capable of providing the required data.

In addition to providing effective treatment to individuals with motor disabilities, it is desirable to gain a further understanding of neurological processes taking place in the CNS. It is generally agreed that limb movements provide an ideal paradigm for understanding how sensory information is converted into coordinated motor behavior (Soechting et al., 1992). In particular, visual-guided reaching movements has become an important paradigm to study how regions of the brain, such as primary motor cortex (MI), are involved in the planning and control of voluntary movement (Caminiti et al., 1990; Georgopoulos, 1995; Kalaska et al., 1992; Shen et al., 1997). Not surprisingly, studies with non-human primates indicate that neural activity related to a specific feature of movement covaries with many other movement variables. To dissociate the various parameters of movement, several studies have examined the response patterns of individual cells when reaching movements are performed under different mechanical loads or arm posture (Caminiti et al., 1990; Kalaska et al., 1989; Scott et al., 1997). A consistent finding from these studies is that the directional tuning of many MI cells is modified by load or posture. These results suggest that the activity of cells is not simply related to the direction of hand movement, but may be more related to intrinsic features of the task, such as the joint kinematics or kinetics. However, further progress on interpreting the nature of the discharge patterns of these cells based on features of motor execution are difficult in these studies because neural activity was only related to hand motion.

Thus, the major stumbling block for identifying the nature of the neural representation in MI during reaching movements is the difficulty in directly quantifying and manipulating the mechanics of multi-joint motion. While a number of devices have been proposed to apply loads to the arm during multi-joint movements (Gomi et al., 1996; Shadmehr et al., 1994), these devices are of limited use because the loads are applied through the band.

OBJECT OF THE INVENTION

It is an object of the invention to provide an instrument that attaches to the limb of a subject and allows various conditions of loading to be applied directly to one or more joints of the limb. An instrument according to the invention provides direct quantification and manipulation of the mechanics of multi-joint motion, and facilitates the detection, quantification, and treatment of neural and/or muscular problems associated with impaired movement of the limbs. An instrument according to the invention also provides data for enhancing an understanding of how sensory information is converted into coordinated motor behavior in the central nervous system (CNS) for use with human and non-human primates.

SUMMARY OF THE INVENTION

In accordance with a first aspect of the invention, there is provided an instrument for monitoring the kinesiology of multi-joint limb motion, comprising: a linkage having four links connected at four joints, each joint having articulation about an axis, the four axes of articulation being substantially parallel; limb coupling means for coupling a limb to the linkage, the limb coupling means maintaining alignment of centers of rotation of two joints of the limb with centers of rotation of two joints of the linkage; means for providing a load to at least one of the two joints of the linkage; and means for obtaining data respecting angular position of at least one of the joints of the linkage.

In accordance with a preferred embodiment of the invention, the linkage having four articulating joints is in the configuration of a parallelogram.

According to a second aspect of the invention, there is provided an instrument for monitoring the kinesiology of multijoint limb motion, comprising: a linkage having two links connected at a joint having articulation about a first axis; a second axis defined at a point near the terminus of one of the links, the second axis being substantially parallel to the first axis; limb coupling means for coupling a limb to the linkage, the limb coupling means maintaining alignment of centers of rotation of two joints of the limb with centers of rotation of the first and second axes; means for providing a load to at least one of the axes; and means for obtaining data respecting angular position of at least one of the axes.

According to another aspect of the invention, there is provided a method for detecting a neural and/or muscular problem associated with impaired movement of a limb, comprising providing a linkage having four links connected at four joints, each joint having articulation about an axis, the four axes of articulation being substantially parallel; coupling a limb to the linkage, wherein centers of rotation of two joints of the limb are aligned with centers of rotation of two joints of the linkage; providing a load to at least one of the two joints of the linkage; and obtaining data respecting angular position of at least one of the joints of the linkage; wherein the data respecting angular position is indicative of a neural and/or muscular problem associated with impaired movement of a limb.

According to yet a further aspect of the invention, there is provided a method for monitoring a neural and/or muscular problem associated with impaired movement of a limb, comprising: providing a linkage having four links connected at four joints, each joint having articulation about an axis, the four axes of articulation being substantially parallel; coupling a limb to the linkage, wherein centers of rotation of two joints of the limb are aligned with centers of rotation of two joints of the linkage; providing a load to at least one of the two joints of the linkage; and obtaining data respecting angular position of at least one of the joints of the linkage; wherein the data respecting angular position is related to status of the neural and/or muscular problem associated with impaired movement of a limb.

According to yet a further aspect of the invention, there is provided a method for treating a neural and/or muscular problem associated with impaired movement of a limb, comprising: providing a linkage having four links connected at four joints, each joint having articulation about an axis, the four axes of articulation being substantially parallel; coupling a limb to the linkage, wherein centers of rotation of two joints of the limb are aligned with centers of rotation of two joints of the linkage; providing a load to at least one of the two joints of the linkage; and obtaining data respecting angular position of at least one of the joints of the linkage; wherein the data respecting angular position is related to progress of the neural and/or muscular problem associated with impaired movement of a limb.

According to yet a further aspect of the invention, there is provided a method for detecting a neural and/or muscular problem associated with impaired movement of a limb, comprising: providing a linkage having two links connected at a joint having articulation about a first axis; defining a second axis at a point near the terminus of one of the links, the second axis being substantially parallel to the first axis; coupling a limb to the linkage such that centers of rotation of two joints of the limb are maintained in alignment with centers of rotation of the first and second axes; and providing a load to at least one of the axes; and obtaining data respecting angular position of at least one of the axes; wherein the data respecting angular position is indicative of a neural and/or muscular problem associated with impaired movement of a limb.

According to yet a further aspect of the invention, there is provided a method for monitoring a neural and/or muscular problem associated with impaired movement of a limb, comprising: providing a linkage having two links connected at a joint having articulation about a first axis; defining a second axis at a point near the terminus of one of the links, the second axis being substantially parallel to the first axis; coupling a limb to the linkage such that centers of rotation of two joints of the limb are maintained in alignment with centers of rotation of the first and second axes; and providing a load to at least one of the axes; and obtaining data respecting angular position of at least one of the axes; wherein the data respecting angular position is indicative of status of the neural and/or muscular problem associated with impaired movement of a limb.

According to yet a further aspect of the invention, there is provided a method for treating a neural and/or muscular problem associated with impaired movement of a limb, comprising: providing a linkage having two links connected at a joint having articulation about a first axis; defining a second axis at a point near the terminus of one of the links, the second axis being substantially parallel to the first axis; coupling a limb to the linkage such that centers of rotation of two joints of the limb are maintained in alignment with centers of rotation of the first and second axes; providing a load to at least one of the axes; and obtaining data respecting angular position of at least one of the axes; wherein the data respecting angular position is indicative of progress of the neural and/or muscular problem associated with impaired movement of a limb.

According to yet a further aspect of the invention, an instrument according to the invention is employed as an exercise and/or rehabilitation device to improve motor performance.

BRIEF DESCRIPTION OF THE DRAWINGS

Embodiments of the invention will now be described, by way of example, with reference to the accompanying drawings, wherein.

DETAILED DESCRIPTION OF THE INVENTION

Figure 1:
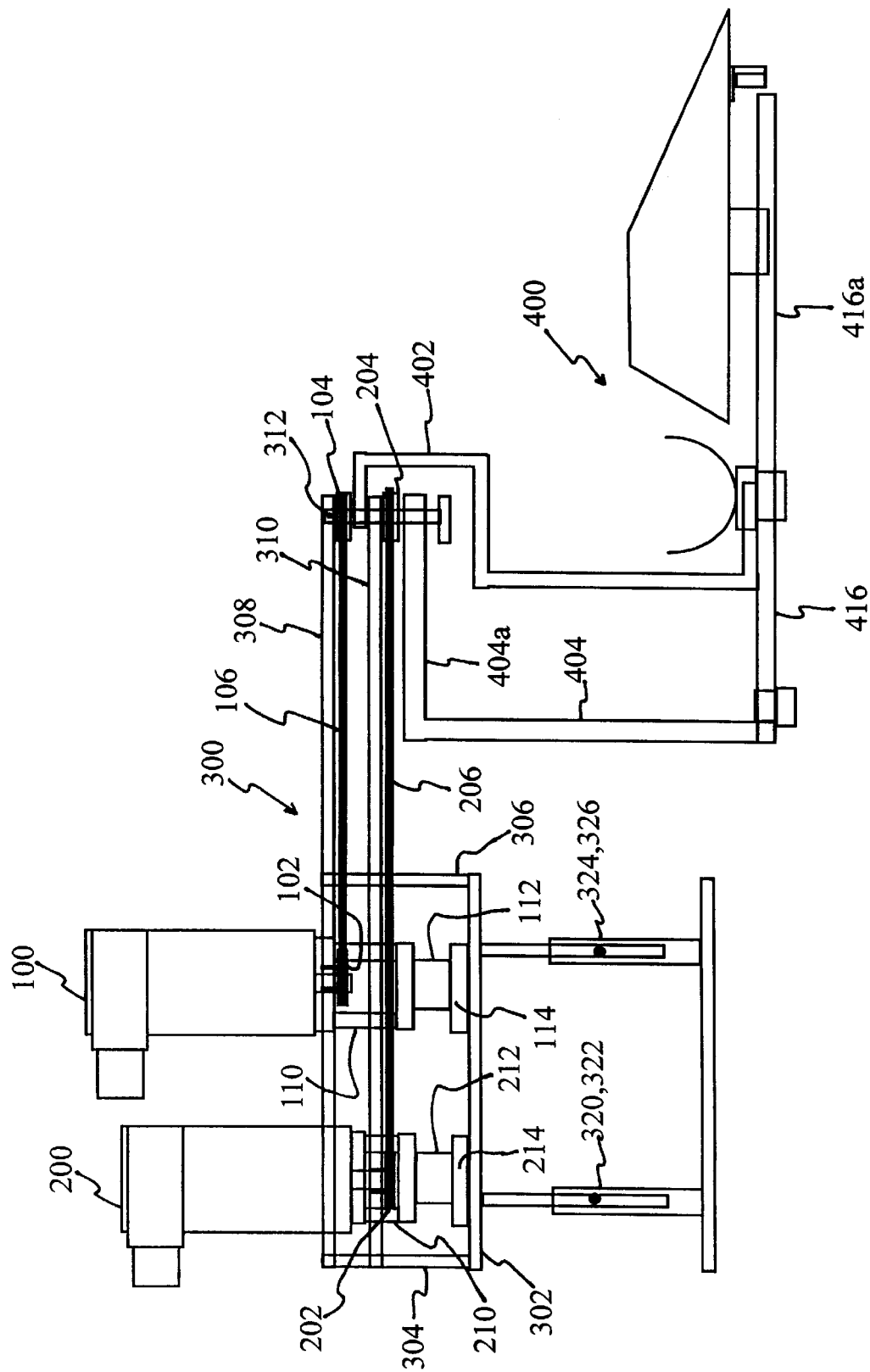
FIG. 1 is a side view of a kinesiological instrument according to a preferred embodiment of the invention.

Standard clinical assessments of multi-joint tasks and joint function do not provide quantitative, objective measures and are inadequate for identifying many abnormalities in neural and muscular disorders. There is a need for reliable quantitative measures of joint kinetics and kinematics to supplement traditional clinical measures. An instrument according to the present invention enhances understanding and provides for the diagnosis and treatment of a wide range of neural and muscular dysfunction. Using the invention, a wide range of features of the motor system can be evaluated, including properties of the musculoskeletal system and the strategies and ability of the CNS to control and coordinate limb movements. Further, use of the invention provides for the evaluation of subjects to develop quantitative standards of normal subjects and provides measures of motor deficits of various patient populations. The results form the basis for programs directed towards, for example, treatment of these disorders, and on-going evaluation of the effectiveness of therapeutic treatment interventions.

Comprehensive neural and muscular assessments that can be carried out in accordance with the invention include: static and dynamic joint mechanical properties such as joint stiffness and viscosity; evaluation of the performance and error associated with goal directed position and force control tasks; reflex responses to perturbations during posture and movement and the role of the stretch and unloading reflex in performance tasks; muscle activation and control strategies to perform simple and complex motor tasks involving changing loads or changing joint mechanical properties; cooperative action of multiple joints such as the shoulder and elbow to generate goal-directed movements; and range of motion of joints and strength.

Visual-guided reaching tasks have become an important paradigm for studying how regions of the brain, such as primary motor cortex, are involved in planning and controlling movement (Georgopoulos, 1995; Kalaska et al., 1992). These multi-joint tasks require visual information to be converted into motor patterns at the shoulder and elbow joints to move the hand through space. Force generated by a muscle influences the motion at both spanned and non-spanned joints making the selection and coordination of motor patterns of the musculature a formidable task dependent on many mechanical and arm geometric variables. Due to the difficulties of monitoring the kinematics of multi-joint motion, a common approach for interpreting neural activity in areas such as primary motor cortex has been to relate the activity of neurons to the direction of hand movement. While simplifying the collection of experimental data, this approach precludes understanding the potential contribution of neural activity in these brain regions to motor execution at the proximal arm joints.

The present invention provides the basis for a paradigm to study how the musculoskeletal system is used to generate coordinated multi-joint motor tasks and how the brain plans and controls these tasks. In particular, using the present invention normal and abnormal motor function can be compared and contrasted. Various sensors on an instrument in accordance with the invention measure a wide range of kinematic and kinetic variables related to, for example, the shoulder, elbow and hand, that allow one to define coordinated limb movement at many different levels of complexity. An instrument in accordance with the invention provides a unique way of manipulating the mechanical conditions of each joint of a limb under investigation independently, since mechanical loads are applied by a mechanical linkage directly to, for example, the arm and forearm. The ability to manipulate visual and proprioceptive information on limb position using the inventive instrument together with a virtual target projection system also provide a valuable tool for investigating neural computations related to body position sense and kinesthesia. The invention can be used to study the activity of proximal arm muscles of subjects performing reaching movements under different loads, and to record the activity of various brain regions (e.g., electroencephalograph (EEG)) when appropriate recording apparatus is used.

The present invention can be used to monitor and manipulate the mechanics of multi-joint arm movements in subjects, and is particularly valuable for studies related to motor rehabilitation. Present diagnostic and clinical assessments of multi-joint motor skills rely predominantly on qualitative descriptions of movement, such as visually verifying whether a subject can repeatedly touch their finger to their nose (O'Sullivan et al., 1994; Van Deusen et al., 1997). These assessments provide only a coarse, subjective measure of motor function. Moreover, they provide no information about the subject's ability to adapt motor patterns to changes in mechanical loads, necessary for normal motor function. The present invention provides a range of quantitative information on the kinematics and kinetics of limb movement under various mechanical conditions which are valuable as a diagnostic and ongoing assessment tool for various motor disorders.

An instrument according to the invention is a mechanical linkage that attaches to a subject's limb. When attached to a limb, the linkage allows the subject to make combined flexion and extension movements of the joints to move the limb in a single plane. The linkage is adjustable so that its joints can be aligned with the centers of rotation of the limb joints under investigation. Suitable couplings such as straps, either alone or in combination with braces or the like, are used to secure the subject's limb to the mechanical linkage. The invention provides the ability to manipulate directly the mechanical characteristics of the joints of a limb under investigation.

The contents of all references and published patents cited throughout this application (including the "Background" Section) are hereby expressly incorporated by reference.

EXAMPLE 1

The following example describes a preferred embodiment of the invention, wherein the linkage is configured to attach to the upper arm and forearm of a subject. In the present example, the subject was a juvenile male monkey (6.5 kg) trained to wear the inventive instrument and perform a variety of multi-joint motor tasks, including reaching movements with and without viscous loads and postural tasks when intermittent or constant torque loads were applied by the device. Because of the similarity between human and non-human primate neural and musculoskeletal systems, subjects such as monkeys are appropriate subjects for experiments investigating problems in multi-joint motor tasks in humans. This similarity renders an instrument in accordance with the invention suitable for use with both humans and non-human primates. Of course, the instrument must be appropriately sized (i.e., scaled) for use with either human or non-human primate subjects.

This example demonstrates how an instrument in accordance with the invention is used to study the kinematics and kinetics of limb movement of individuals performing multi-joint tasks under various loads. Although the subject (monkey) did not have any known motor disorders, it will be appreciated from the results of the present example that an instrument in accordance with the invention is a valuable diagnostic and ongoing assessment tool for various motor disorders.

Apparatus

Figure 2:
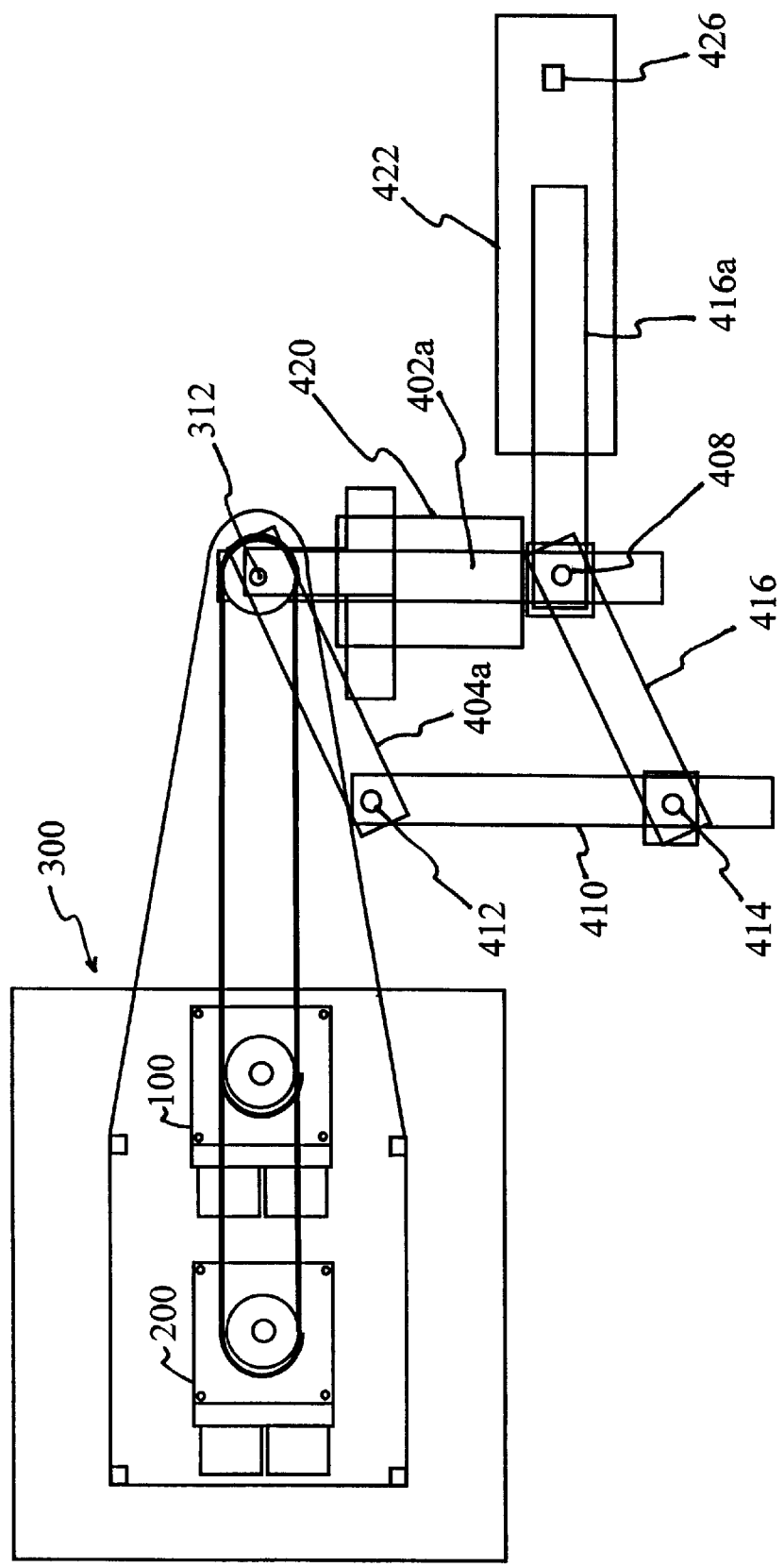
FIG. 2 is a plan view of the embodiment shown in FIG. 1.
Figure 3:
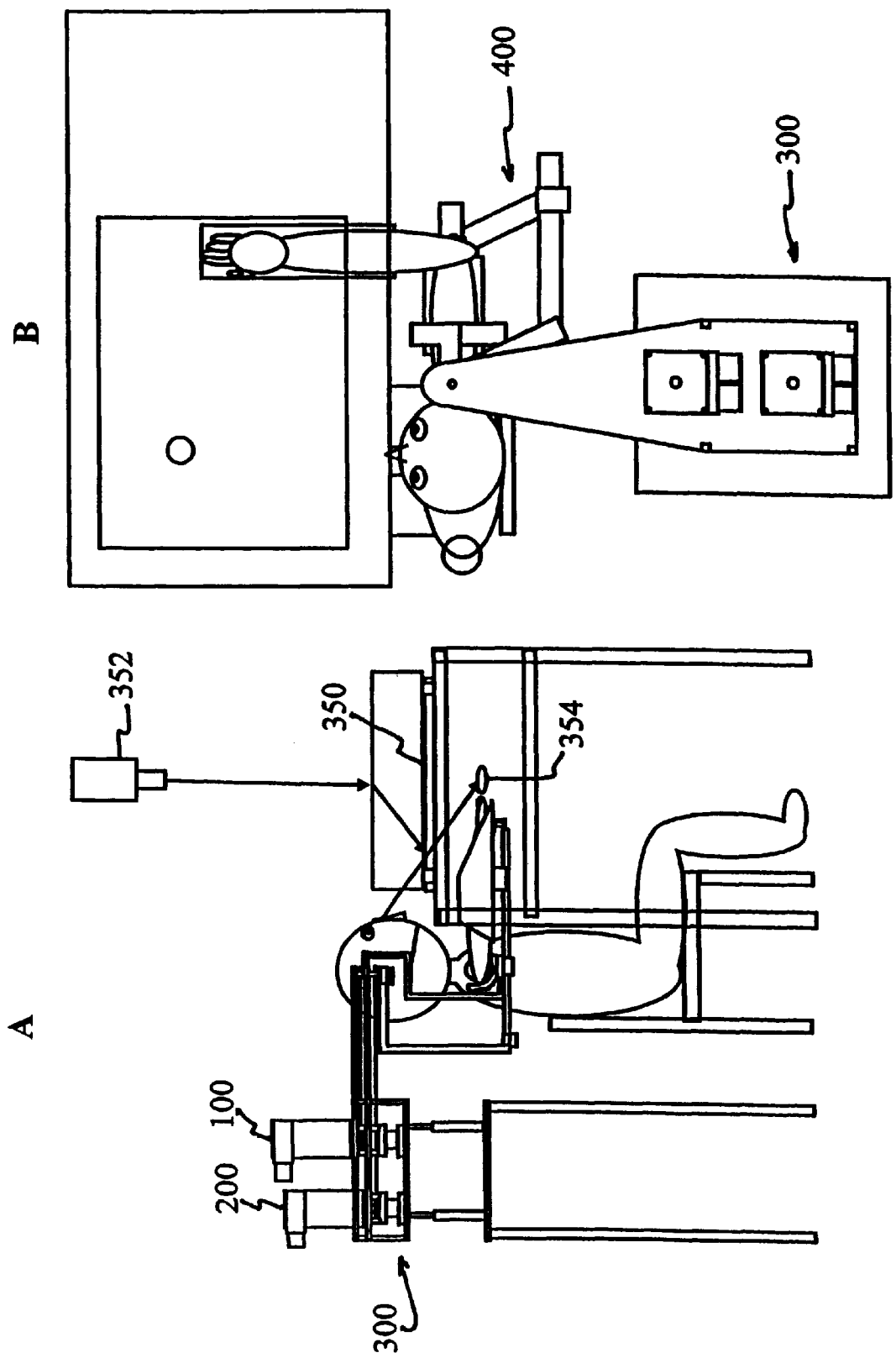
FIGS. 3A and 3B are side and plan views, respectively, of the embodiment shown in FIG. 1, additionally showing a subject using the embodiment and a computer projection system for presenting virtual targets to the subject.

According to the preferred embodiment, there is provided a mechanical linkage that attaches to the upper arm and forearm of a subject (see FIGS. 1 to 3). The mechanical linkage allows the subject to make combined flexion and extension movements of the shoulder and elbow joints to move his/her hand to targets in the horizontal plane. The linkage is attached by one of its articulating joints to a rigid structure such as a housing or a support that places it in proper alignment with the subject In the case of an arm, proper alignment is achieved when the center of rotation of that articulating joint is aligned with the center of rotation of the subject's shoulder. The rigid structure effectively anchors the linkage to a fixed point in space, allowing the linkage to be manipulated about that point, and, when the subject to which the linkage is attached is also held stationary by remaining in a suitable position, such as sitting, any relative movement between the subject's shoulder and that articulating joint is minimized. It is preferred that friction in the joints of the linkage be -minimized, and to this end, ball bearings, bushings, or the like are employed at each joint. The linkage is adjustable so that its joints can be aligned with the centers of rotation of the shoulder and elbow joints of the subject's arm. Couplings attached to the linkage secure the upper arm and forearm to the linkage. If desired, the couplings may be padded with a suitable material such as closed-cell foam, to improve the subject's comfort.

According to the preferred embodiment, mechanical characteristics of the shoulder and elbow joints can be manipulated directly. As shown in FIGS. 1 and 2, first and second torque motors 100,200 (Compumotor SM232A motor, APEX10 motor driver, AT6450 programmable control card) are employed, and timing belts 106,206 connect each motor to the mechanical linkage, generally denoted by reference numeral 400, such that the first motor 100 acts on the upper arm and the second motor 200 acts indirectly on the forearm. Loads at the elbow joint are applied by the second motor 200, whereas loads at the shoulder are applied by the combined action of both motors 100,200. A main computer (not show) electrically connected to the motors 100,200 via the programmable control card controls the motors and reads data from them.

The motors 100,200 are mounted on a housing generally designated by reference numeral 300 having a bottom plate 302, side portions 304, 306, and upper and lower plates 308, 310. The plates 308, 310 extend substantially beyond one side 306 of the housing 300, and the upper plate 308 overlies the lower plate 310 at least in an area where an axle 312 is disposed therethrough. As the plates are substantially cantilevered beyond the housing 300, and they support and anchor the linkage 400 to a fixed point it is important that they are strong and rigid, hence they are preferably made from a plate material such as steel or aluminum.

The linkage 400 is attached to the axle 312 via first and second vertical members 402, 404. These members are referred to as being vertical, although as can be seen from FIG. 2, each member has at least one vertical section and at least one horizontal section. In particular, vertical member 402 has a substantial horizontal section 402a, and vertical member 404 has a substantial horizontal section 404a. The vertical members 402,404 have a common axis of rotation defined by the axle 312. Each of these members 402,404 is independently connected to the axle 312 via a ball-bearing race, bushing, or other suitable low-friction device, such that each member 402,404 can rotate freely and independently on the axle 312. The bends in the first vertical member 402 prevent it from contacting the second member 404 when a limb, attached to the linkage 400, moves through its range of movement.

The motors 100,200 are mounted on reaction torque sensors 112,212 (Transducer Techniques, TRT-50) via suitable support platforms 110,210, so that forces generated by the motors can be measured. Data is read from the sensors 112,212 by the main computer. The reaction torque sensors 112,212 are attached to the bottom plate 302 of the housing 300. If desired, the sensors 112,212 may be attached to the bottom plate 302 via sliding plates 114,214 which, when loosened, allow the motors 100,200 to be moved on the bottom plate 302, to facilitate changing of timing belts 106,206 and adjustment of belt tension. Mounting of the motors 100,200 on their respective support platforms 110, 210 is such that the first motor 100 is disposed above the upper top plate 308, and the second motor 200 is disposed above the lower top plate 310. Moreover, in this configuration the shaft of the first motor 100 protrudes through the upper plate 308. A gear 102, such as a toothed gear, is disposed on the shaft of motor 100, and is connected to a second gear 104 disposed on the axle 312 via a timing belt 106. The second gear 104 is fixed to the first vertical member 402. Similarly, the shaft of the second motor 200 protrudes through the lower plate 310. A gear 202, such as a toothed gear, is disposed on the shaft of motor 200, and is connected to a second gear 204 disposed on the axle 312 via a timing belt 206. The second gear 204 is fixed to the second vertical member 404. In this manner motor 100 drives and/or is driven by member 402, and motor 200 drives and/or is driven by member 404.

The first and second vertical members 402,404 connect the rest of the linkage 400 to the motors 100,200. With reference to FIG. 2, it can be seen that the linkage 400 is essentially a four-bar linkage, the four bars being links 402a, 404a, 410, and 416. All these links lie in a substantially horizontal plane, although the plane of link 404a is elevated above that of the remaining three links 402a, 410, and 416, as can be seen in FIG. 1. Preferably, the linkage 400 is very strong and rigid yet light-weight, and material such as aluminum alloy, or other light, strong metals, or other materials such as carbon fiber, are advantageously used. The first vertical member 402 and horizontal link 402a are joined together and they may be a solid continuous structure formed by any suitable technique, such as by welding, casting, or machining. The first vertical member 402 and link 402a may also be formed as separate components and joined by screws or the like, so long as a rigid structure is provided. Similarly, the second vertical member 404 and link 404a are also a rigid structure. Link 402a has a movable ball-bearing joint 408 removably disposed thereon. The movable ball-bearing joint 408 can be moved and fixed in place, using thumb-screws, set-screws, a clamping mechanism, or the like, at any location along the length link 402a. If desired, detents, graduations, or any other markings for indicating the position of the movable ball-bearing joint can be provided on link 402a.

The second vertical member 404 is attached to link 410 with a ball-bearing joint 412. Link 410 is substantially parallel to link 402a, and also has a movable ball-bearing joint 414 removably disposed thereon. As discussed above in respect of link 402a, markings can also be provided on link 410 to indicate the position of the movable ball-bearing joint. The fourth link 416 is attached to links 410 and 402a via the movable ball-bearing joints 414,408, and is substantially parallel to the horizontal section 404a of the second vertical member 404. Section 416a of link 416 extends beyond movable joint 408. As discussed above with respect to vertical member 402 and link 402a, link 416 and section 416a are also a rigid structure formed as a single unit or from separate pieces joined together.

It was stated above that pairs of links 410 and 402a, and 416 and 404a, are each substantially parallel, and in this configuration the linkage is essentially a parallelogram (i.e., a quadrilateral having both pairs of opposite sides parallel to each other). It will be appreciated that, using the movable joints 408,414, it is possible to achieve configurations of the linkage 400 in which this parallelism is not maintained. While the linkage will work in such non-parallel configurations, it is preferred that each of these pairs of links be maintained parallel. This is because, when parallelism is maintained, relationships between the forces and motions generated at the linkage 400 and those indicated by the motors 100,200 are linear. When parallelism is lost, these relationships become nonlinear. The below equations of motion used to calculate the muscular torque generated at the limb joints (e.g., shoulder and elbow) assume parallelism of the linkage. Accordingly, when adjusting the position of movable joint 408 on link 402a, the same adjustment must be made for movable joint 414 on link 410 to maintain parallelism.

In use, the instrument is positioned such that the center of rotation of a subject's shoulder is directly below the ball-bearing axle 312, as shown in FIGS. 3A and 3B. Link 402a and section 416a of link 416 each have a coupling 420, 422 or suitable structure for holding the upper arm and forearm, respectively, of a subject in place above those links. Straps having buckles, Velcro™ closures, or the like, secure the upper arm and forearm in the couplings 420,422. The positions of couplings 420,422 are adjustable along the lengths of the respective links 402a,416a, to accommodate different-sized subjects. Two accelerometers 426 (Entran, EGAXT-5) are attached to link 416a or to the coupling 422 just below the position of the subject's hand. The accelerometers are electrically connected to the main computer and provide hand acceleration information.

The entire instrument is conveniently attached to a mechanism which provides for easy adjustment of the instrument's height and position relative to a subject being tested. As shown in FIG. 1, the instrument can be attached to a stand having a rack and pinion, or, for example, four telescoping pillars 320, 322, 324, 326 (two are shown in FIG. 2), which can be raised or lowered and locked in position, thus providing an appropriate height for any subject.

As can be seen from FIGS. 1 to 3 and the above description, when the arm of a subject is secured to the linkage 400, the subject can move his/her arm through a wide range of movement within the horizontal plane. This movement may be performed without any loading of any joints of the arm, i.e., with the linkage moving freely. Information concerning arm movements (i.e., joint angular position) is provided by encoders built in to the Compumotor torque motors used in the present example. The encoders (not shown) are electrically connected to the main computer and provide angular position information (i.e., angular position of the motor shaft as it rotates about its axis). The first motor 100 provides direct feedback of shoulder joint angle. Elbow joint angle is computed by subtracting the encoder signal obtained from motor 100 from the encoder signal from the second motor 200. Hand position is calculated using trigonometry from shoulder and elbow joint angles and the measured length of the subject's upper arm and forearm/hand lengths. Of course, the motors are used to provide loading, such as viscous loading, specifically to the shoulder and/or the elbow joints, and the same information regarding joint angles and positions can be obtained under loaded or unloaded conditions.

As mentioned above, this example involves the subject performing reaching tasks toward targets, in this case targets in the horizontal plane. A computer projection system for presenting virtual targets to the subject is suitable, as shown generally in FIG. 3. Briefly, target information generated by the main computer is transferred to a $2^{nd}$ computer (not shown) which displays virtual targets 354 in the task plane (e.g., horizontal plane) using a semi-transparent mirror 350 and a projection monitor 352, as is known in the art (Goodbody et al., 1998; Turner et al., 1995).

According to the invention, the main computer reads data from various sensors on the instrument and provides measures of a number of kinesiological variables of movement, based on, for example, the equations defined below. Of the various sensors and corresponding data, that can be obtained, data relating to joint angular position are most important for kinetic and kinematic studies of limb movements. According to the preferred embodiment, joint angular position is obtained from the motor encoders with a resolution of, for example, 8192 units per revolution. Hand position is computed from the joint angles using trigonometry, while hand acceleration is measured by the two linear accelerometers 426 attached to the linkage 400 just below the hand. The magnitude of torque applied to the mechanical linkage 400 by each motor is monitored using the reaction torque sensors 112,212 attached to the base of the motors 100,200. It will be appreciated that the invention can be combined with other known techniques and equipment to obtain further information about limb movement during motor tasks. For example, the activity of proximal arm muscles can be measured when the invention is used with suitable electromyography (EMG) equipment and techniques.

Equations of Motion

Figure 4:
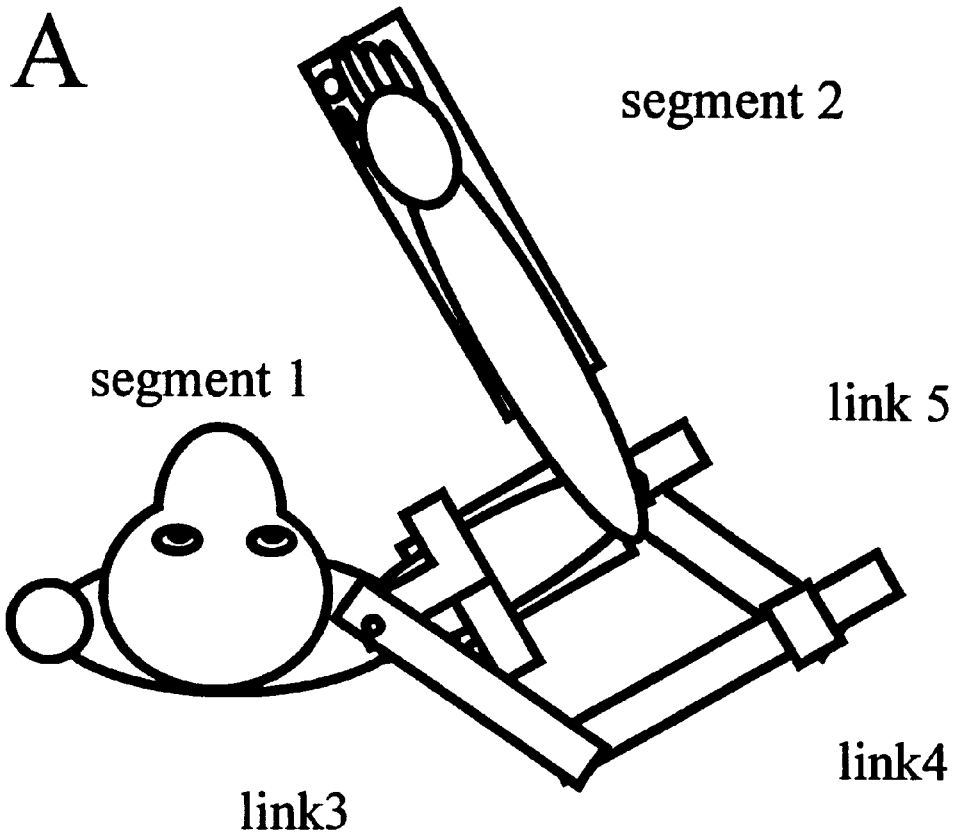
FIG. 4A is a simplified drawing of a subject (a monkey) attached to the embodiment shown in FIG. 1.
FIG. 4B shows the subject's arm modelled as two segments, the upper arm and the forearm/hand, with single degree-of-freedom joints at the shoulder and elbow joints.
FIGS. 4C and 4D show how the equations of motion divide the four-bar linkage into two two-joint systems, one including the arm and forearm of the subject (segments 1 and 2) and the other including the posterior bars of the linkage.
Figure 4:
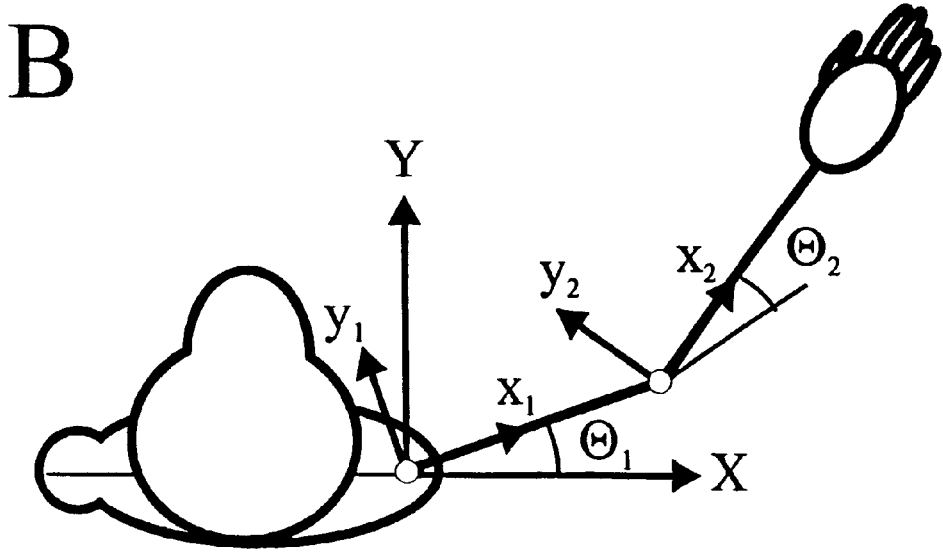
Figure 4:
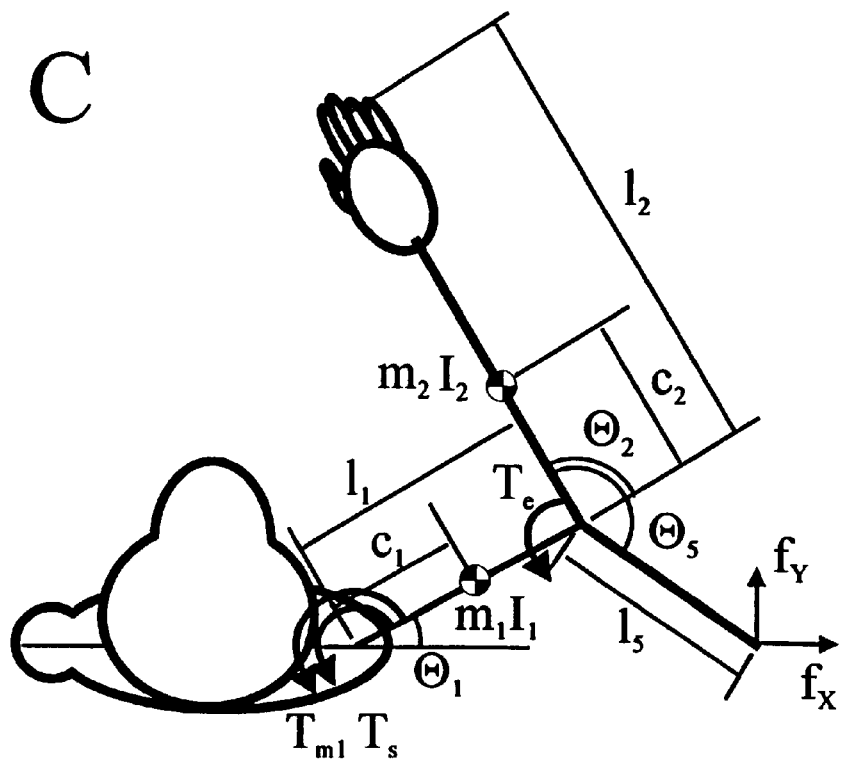
Figure 4:
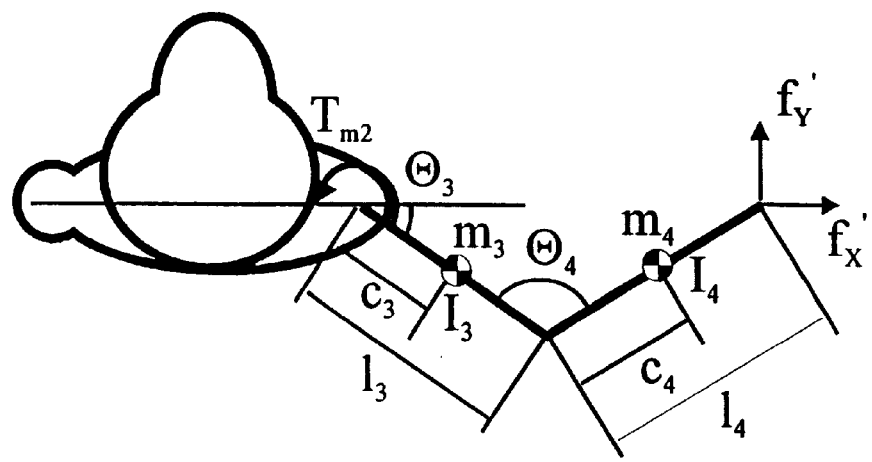

The following equations are defined with reference to FIG. 4. Terms and symbols used in the below equations are defined as follows:

Terms

| | |
|---|---|
| c | distance from center of mass to proximal end of segment/link |
| d,g,h | static and dynamic friction constants |
| f | contact force on link 5 |
| f' | contact force on link 4 |
| I | moment of inertia |
| l | length of link |
| m | mass of a link |
| T | Torque |
| $\Theta,\dot{\Theta},\ddot{\Theta}$ | Angular position, velocity and acceleration |

Subscripts

| | |
|---|---|
| 1–5 | segment/link 1 to 5 |
| e | elbow joint of monkey |
| s | shoulder joint of monkey |
| m1 | motor 100 |
| m2 | motor 200 |
| x,y | cartesian coordinates (local) |
| X,Y | cartesian coordinates (global) |

The time-varying net muscular torque generated at the shoulder and elbow can be estimated during limb movements given the kinematics of the joints, and the length, mass and inertial characteristics of the instrument and the subject's arm. In the present example, the monkey's arm was modelled as two segments, the upper arm and the combined forearm and hand, with single degree-of-freedom joints at the shoulder and elbow. Motion of the shoulder and elbow is defined by relative angles between the two adjacent segments (FIG. 4B). Flexor angular motion and torque are both defined as positive, whereas extensor terms are negative. Previous studies have documented the equations of motion for a two-joint system to describe planar limb motion (Hollerbach et al., 1982; Karst et al., 1991). In the present situation, the equations of motion must also consider the properties of the four-bar linkage 400 and the two torque motors 100,200. For the description of these equations, the term "link" defines a rigid component of the linkage, the term "body segment" defines the upper arm or forearm/hand of the subject, and the term "segment" defines the combined properties of a link attached to a body segment. For example, segment 1 represents the combined properties of link 1 and body segment 1. Also, in FIG. 4A and the below equations, links 402a, 416a, 404a, 410, and 416 have been renumbered 1, 2, 3, 4, and 5, for simplicity.

To simplify the equations, links 3 and 4 connecting the second motor 200 to the forearm (FIG. 4D) are treated separately as a two-link system and are described by:

$$T_{m2}=(I_{m2}+I_3+I_4+m_3c_3^2+m_4(l_3^2+c_4^2+2l_3c_4\cos\Theta_4))$$
$$\Theta_{33}+(I_4+m_4c_4^2+m_4l_3c_4\cos\Theta_4)\Theta_4-(m_4l_3c_4\sin\Theta_4)$$
$$\dot{\Theta}_4^2-(2m_4l_3c_4\sin\Theta_4)\dot{\Theta}_3$$
$$\dot{\Theta}_4-(l_3\sin\Theta_3+l_4\sin(\Theta_3+\Theta_4))f'_x+(l_3\cos\Theta_3+l_4\cos(\Theta_3+\Theta_4))f'_y+d_{m2}($$
$$\dot{\Theta}_3/abs(\dot{\Theta}_3))+g_{m2}\tanh(\dot{\Theta}_3h_{m2}) \quad (1)$$

$$0=(I_4+m_4c_4^2+m_4l_3c_4\cos\Theta_4)\Theta_3+(I_4+m_4c_4^2)\Theta_4+(m_4l_3c_4\sin\Theta_4)$$
$$\dot{\Theta}_3^2-l_4\sin(\Theta_3+\Theta_4))f'_x+l_4\cos(\Theta_3+\Theta_4)f'_y \quad (2)$$

The various terms are defined in FIG. 4 and as indicated above. These equations can be solved for $f'_x$ and $f'_y$, the contact force from link 5 onto link 4 of the linkage. The equations of motion for segments 1 and 2 can be solved using:

$$T_s=(I_{mI}+I_1+I_2+m_1c_1^2+m_2(l_1^2+c_2^2+2l_1c_2\cos\Theta_2))$$
$$\Theta_1+(I_2+m_2c_2^2+m_2l_1c_2\cos\Theta_2)\Theta\times_2-(m_2l_1c_2\sin\Theta_2)$$
$$\dot{\Theta}_2^2-(2m_2l_1c_2\sin\Theta_2)\dot{\Theta}_1\dot{\Theta}_2-(l_1\sin\Theta_1 l30\ l_5\sin(\Theta_1+\Theta_2-\Theta_5))f_x+$$
$$(l_1\cos\Theta_1+l_5\cos(\Theta_1+\Theta_2-\Theta_5))f_y-T_{mI}+d_{mI}(\dot{\Theta}_1/abs(\dot{\Theta}_1))+g_{mI}\tanh($$
$$\dot{\Theta}_1h_{mI}) \quad (3)$$

$$T_e=(I_2+m_2c_2^2+m_2l_1c_2\cos\Theta_2)\Theta_1+(I_2+m_2c_2^2)\Theta_2+(m_2l_1c_2\sin\Theta_2)$$
$$\dot{\Theta}_1^2-l_5\sin(\Theta_1+\Theta_2-\Theta_5))f_x+l_5\cos(\Theta_1+\Theta_2-\Theta_5)f_y+d_2(\dot{\Theta}_2/abs(\dot{\Theta}_2))(4)$$

where $$f_x=-f'_x \text{ and } f_Y=-f'_Y \quad (5)$$

The morphometric parameters for segments 1 and 2 in equations 3 and 4 represent the combined values for the subject's limb segments with those for the associated segments of the linkage. The constants for the static and dynamic friction terms generated by the mechanical linkage 400 and motors 100,200 were defined from direct measures of motion of the mechanical linkage 400 (without the monkey) as torque pulses were applied by the motors 100,200. The terms were identified based on the relationship between motor torque and angular motion at one joint while the other joint was fixed and unable to rotate. Least squares regressions were used to identify the parameters for both the static and dynamic friction terms.

Data Acquisition System

General purpose data acquisition software (LabVIEW™, National Instruments) running on the main computer was used as a basis for a data acquisition system for the invention. Using this software, a custom data acquisition program was developed. The acquisition program monitors motor encoder position, and controls the motor torque either directly or through downloadable programs to the AT6450 motor control card. Target lights, encoder position and motor commands are updated by the main computer approximately every 4 ms. As mentioned above, target information is transferred to a $2^{nd}$ computer which displays virtual targets in the task plane using a semi-transparent mirror and a projection monitor (Goodbody et al., 1998; Turner et al., 1995). A data acquisition card (National Instruments, AT-MIO64E-3) provides 32 differential analog signals to monitor hand acceleration, motor torque, electromyographic activity as well as the timing of neural firing at 1000 Hz.

The analog and motor signals were analyzed using three basic procedures. First, the analog signals were low passed filtered by removing all frequencies above 100 Hz using a Fast Fourier Transform (FFT). The analog and motor signals were synchronized and re-sampled at 200 Hz. The signals were then filtered at 10 Hz with a low pass Butterworth Filter (Winter, 1990). The mean and standard deviation of the temporal pattern of each signal across repeated trials was determined after aligning each waveform to the onset time of movement defined by the initial deviation of hand acceleration from baseline levels.

Results

Equations 1 through 4 contain more than 40 different variables related to the morphometric properties of the monkey's arm, the mechanical linkage and the torque motors. A test was performed to validate the accuracy of these equations to characterize the mechanics of the linkage by applying 300 ms torque pulses (±0.15 Nm) by either the first motor 100, the second motor 200, or both while monitoring the motion of the linkage when the monkey was not wearing the device. The shoulder and elbow torques were calculated from equations 1 through 4 assuming the inertial properties of the monkey's upper arm and forearm were zero. Since the monkey was not attached to the linkage, the computed muscular torques should be zero. Error in the equations of motion was defined as the root mean square (rms) of the computed shoulder and elbow torques divided by the rms of the torque applied by the motors. Average error across eight torque conditions and three repetitions was 13.9%.

Figure 5:
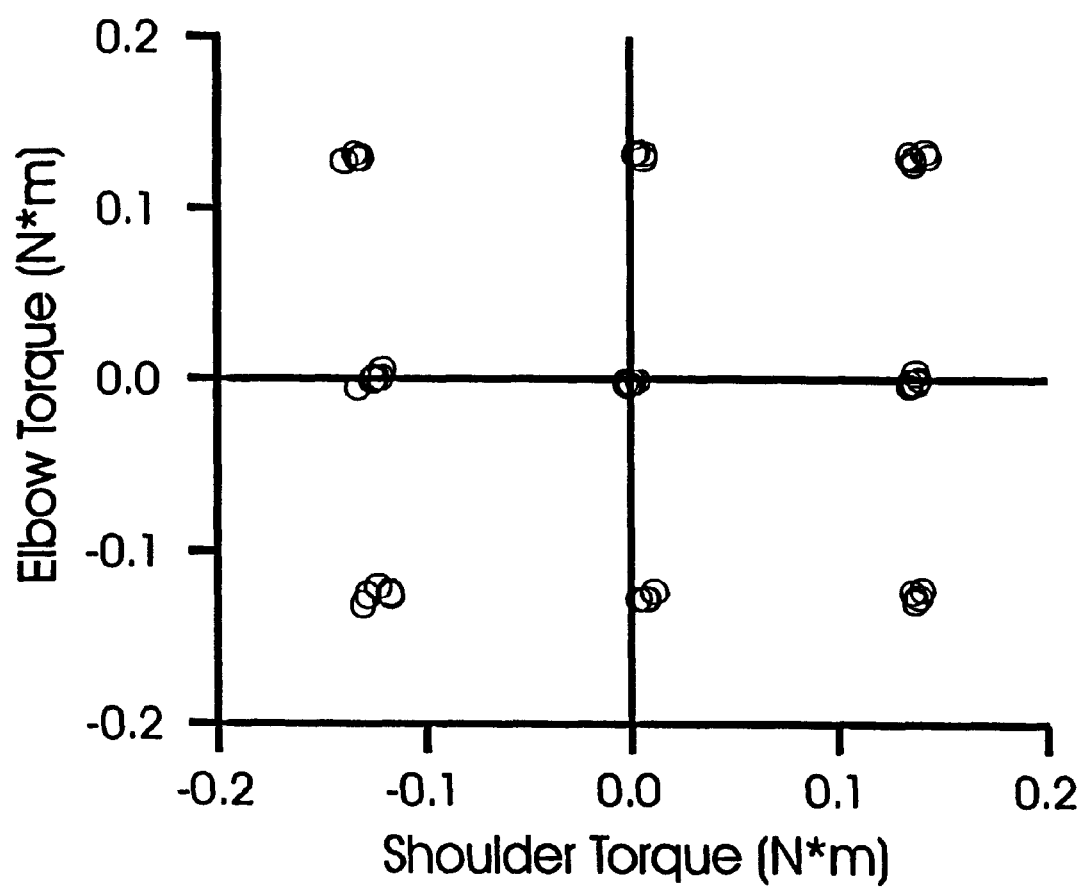
FIG. 5 shows the results of a trial in which the subject (monkey) maintained a similar arm posture with its hand at a central target while the load applied at each joint was independently modified using the embodiment shown in FIG. 1. Each circle denotes the net muscular torques at the shoulder and elbow for one of nine combinations of loads applied (five repeat trials for each condition). Flexion torque is defined as positive.

As mentioned above, the monkey (6.5 kg) was trained to wear the inventive instrument and perform a variety of multi-joint motor tasks, including reaching movements with and without viscous loads and postural tasks when intermittent or constant torque loads were applied by the motors 100,200. FIG. 5 illustrates the net muscular torque at the shoulder and elbow for repeated trials in which the monkey was trained to maintain its hand at a central target while different combinations of flexor and extensor torques were applied by the motors. Each circle denotes the net muscular torques at the shoulder and elbow for one of nine combinations of loads applied by the two torque motors 100,200 (five repeat trials for each condition). Flexion torque is defined as positive. While the device allows mechanical loads to be applied only at the shoulder or elbow during this multi-joint postural task, any combination of loads can also be applied at the two joints, such as a flexor load at the shoulder and an extensor load at the elbow.

Figure 6:
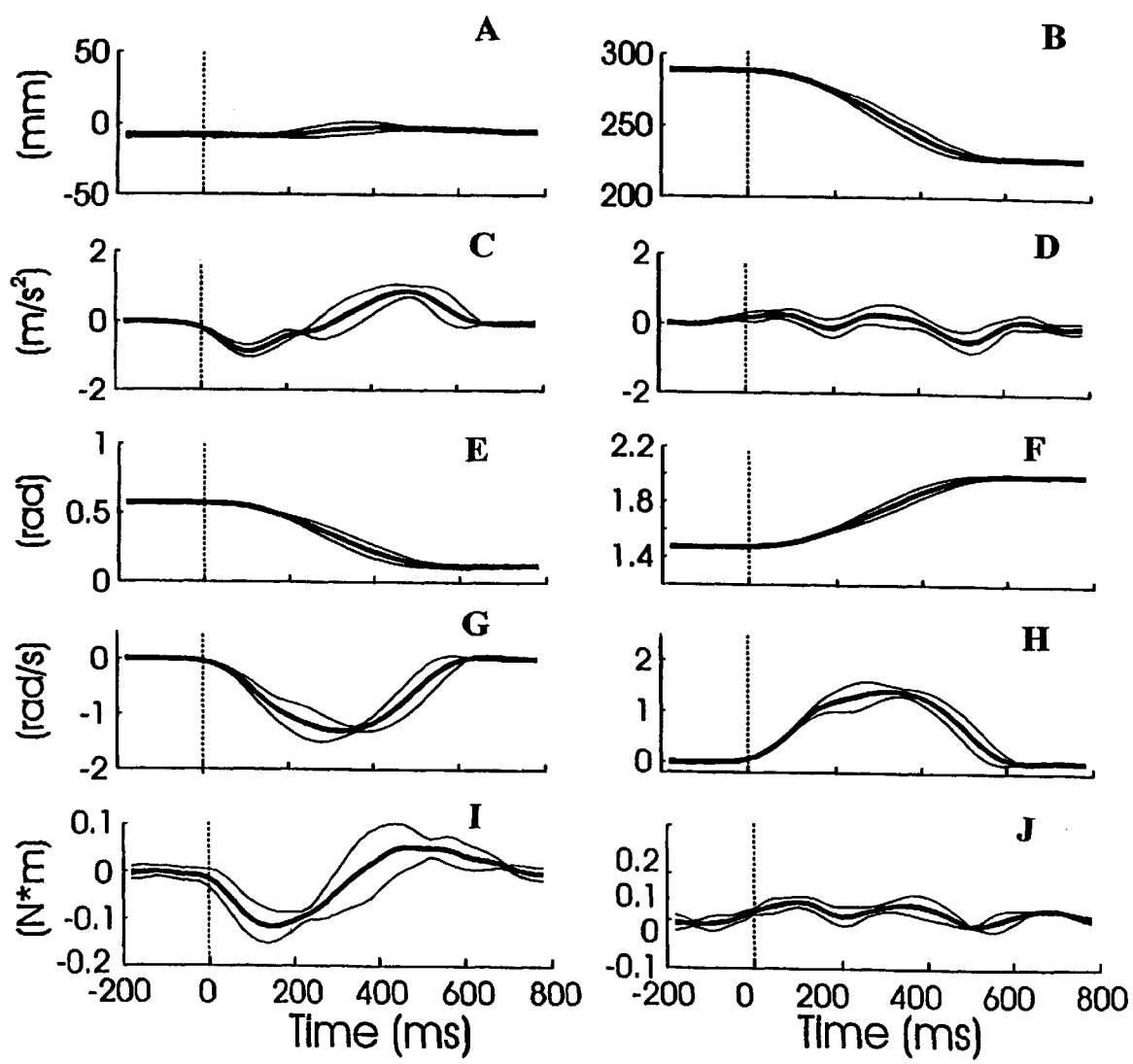
FIG. 6 shows the kinematics and kinetics of limb motion when the subject (monkey) made a 6 cm reaching movement from a central start position to a target located towards itself. The mean (thick line) and standard deviation (thin lines) for each variable are shown for five repeat trials. The vertical dashed line denotes the onset of movement. Flexion motion and torque are both positive. A, Hand Position (X); B, Hand Position (Y); C, Hand Acceleration (Local X); D, Hand Acceleration (Local Y); E, Shoulder Angle; F, Elbow Angle; G, Shoulder Velocity; H, Elbow Velocity; I, Shoulder Torque; J, Elbow Torque.

FIG. 6 illustrates the kinematics and kinetics of the hand, shoulder and elbow joints when the monkey moved 6 cm from a central start position to a peripheral target located near its body. The mean (thick line) and standard deviation (thin lines) for each variable are shown for five repeat trials. The vertical dashed line denotes the onset of movement. Flexion motion and torque are both positive. A shoulder extensor torque (negative) was required to initiate the limb motion followed by a small flexor torque to brake the limb motion at the spatial target. Note that while limb movement involved approximately equal motion at the shoulder and elbow joints, the magnitude of the muscular torques are much larger at the shoulder than at the elbow.

Figure 7:
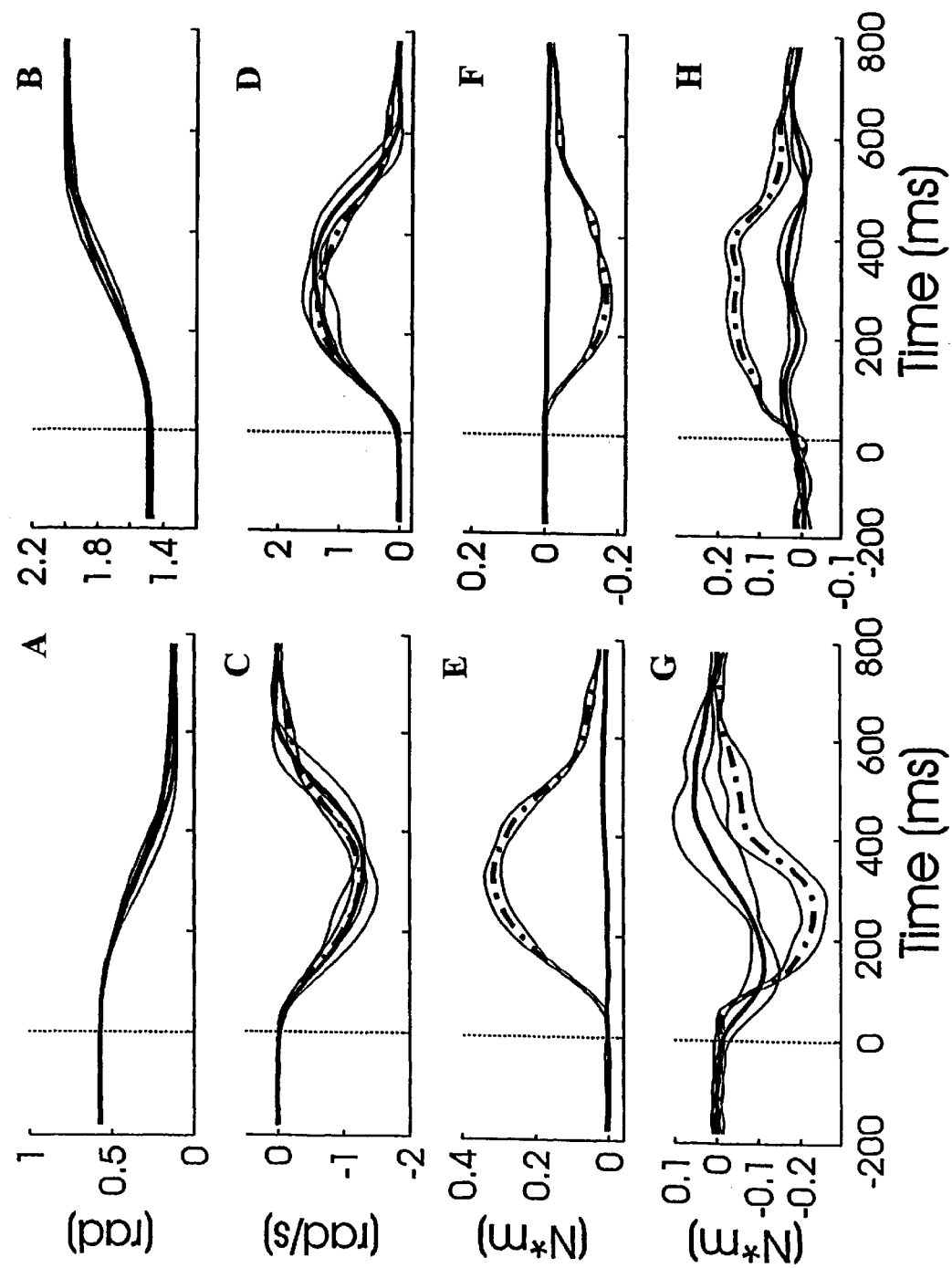
FIG. 7 is a comparison of the kinematics and kinetics of limb motion with (dot-dashed line) and without (solid thick) a viscous load applied to the two joints. Thin lines denote one standard deviation for each respective signal. Movement for the unloaded condition is from FIG. 6. A, Shoulder Angle; B, Elbow Angle; C, Shoulder Velocity; D, Elbow Velocity; E, Motor 1 Torque; F, Motor 2 Torque; G, Shoulder Torque; H, Elbow Torque.

An important feature of the invention is the ability not only to monitor the kinesiology of limb motion, but also to provide dynamic perturbations either at the shoulder or elbow joints. A mechanical load of particular interest for movement studies are viscous loads that act only during movement. Feedback of joint angular velocity can be used to control motor torque to generate viscous loads at each joint. In this situation, the motors generate torque that opposes angular motion, i.e., the faster the movement, the larger the opposing torque. The motors apply no loads when the arm is stationary. When viscous loads are initially applied to the monkey's arm by the inventive linkage, there is a significant alteration in the arm motion including a decrease in movement speed as well as large curvatures in hand trajectory, as seen in human studies where novel loads are applied to the arm (Lackner et al., 1994; Shadmehr et al., 1994). With considerable practice, the monkey makes roughly straight hand trajectories so that reaching movements can be performed with similar kinematic profiles, but with appreciable changes in the muscular torques at the shoulder and elbow (FIG. 7). There is a large increase in the shoulder and elbow torque for movements with viscous loads (dot-dashed) as compared to unloaded conditions (solid). Thin lines denote one standard deviation for each respective signal. Movement for the unloaded condition is from FIG. 6. A braking flexor torque is not required when viscous loads are added because the monkey must continue to apply and extensor torque to the end of movement to oppose the motor load. A large sustained flexor torque is required at the elbow due to the resistive force from the motors. The benefits of applying these mechanical loads during movement is that the kinetic features of movement which vary between loaded and unloaded conditions are dissociated from the kinematics of limb motion which remain constant. Moreover, the invention allows the magnitude of the changes in joint mechanics to be quantified. An added benefit of studying neural activity when viscous loads are applied is that the net muscular torques to maintain constant are postures are not effected by the dynamic perturbations.

Figure 8:
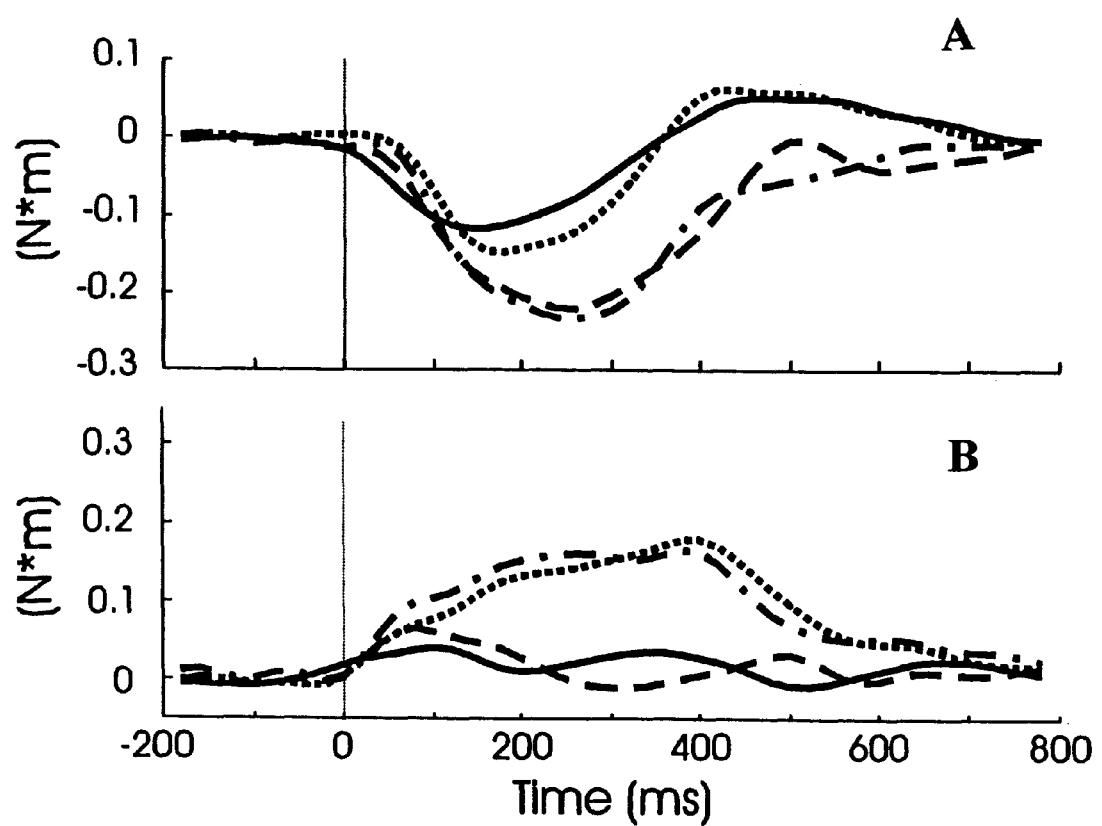
FIG. 8 illustrates that the preferred embodiment shown in FIG. 1 provides viscous loads applied to each joint independently. Shown are the shoulder (A) and elbow (B) torques from FIG. 7 where movements were performed with no loads (solid line) or with viscous loads at both joints (dot-dashed line), and additionally loads applied only at the shoulder (dashed line) and only at the elbow (dotted line). The diagram illustrates only the mean of five repeat trials.

Not only can the mechanics of limb motion be modified under dynamic conditions, but the invention can also selectively modify the mechanics of either the shoulder or the elbow joint independently. FIG. 8 illustrates how the motors 100,200 can be used to create specific changes in the muscular torques at either the shoulder or elbow joints during movement. The solid and dot-dashed lines illustrate shoulder and elbow torques displayed from FIG. 7 for movements performed without any viscous loads and when viscous loads are added to both the shoulder and elbow joints, respectively. When a viscous load is applied at only the shoulder joint, the shoulder muscular torque pattern (dashed line) follows that observed previously when viscous loads were applied at both joints. In contrast, the elbow torque pattern matches that for the unloaded condition. The reverse pattern is observed when a viscous load is applied only at the elbow (dotted line); the elbow torque pattern matches the profile observed when loads were applied at both joints while the shoulder torque pattern follows that observed for unloaded movements. FIG. 8 illustrates only the mean of five repeat trials.

Figure 9:
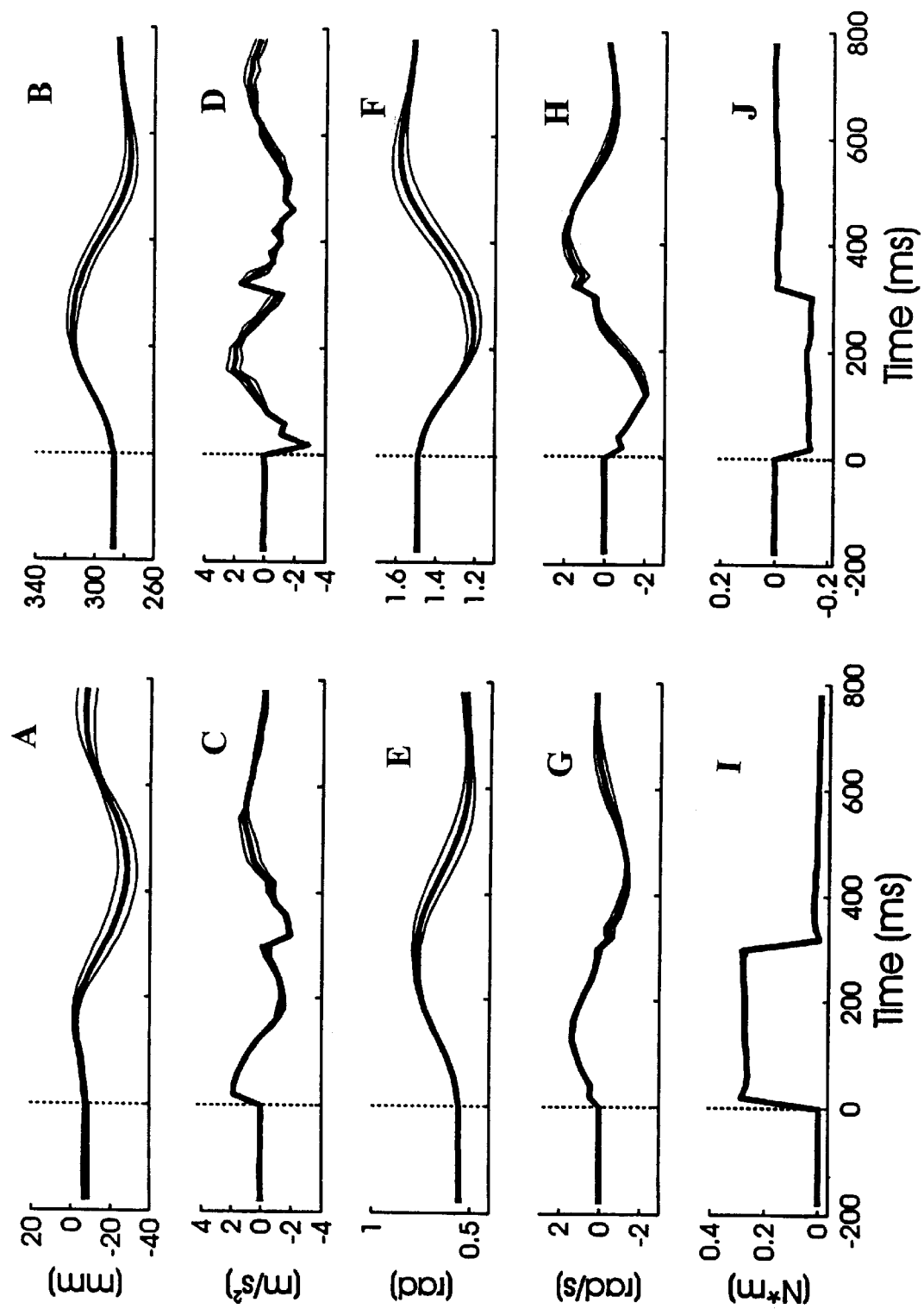
FIG. 9 shows the kinematics of the subject's hand, shoulder and elbow joints when transient torque pulses are applied by the embodiment shown in FIG. 1 (bottom traces). The mean and standard deviation are shown for five repeat trials. The vertical line denotes the start of the torque pulse. A, Hand Position (X); B, Hand Position (Y); C, Hand Acceleration (Local X); D, Hand Acceleration (Local Y); E, Shoulder Angle; F, Elbow Angle; G, Shoulder Velocity; H, Elbow Velocity; I, Motor 1 Torque, Motor 2 Torque.

Another application of the invention is to examine the functional properties of the various spinal and supraspinal reflex systems by applying transient perturbations to the limb of the monkey during static and dynamic tasks. The kinematics of limb motion can be recorded when transient loads are applied by the two torque motors 100,200 (FIG. 9). In FIG. 9 the kinematics of the monkey's hand, shoulder and elbow joints are shown when transient torque pulses are applied by the torque motors 100,200 (bottom traces). The mean and standard deviation are shown for five repeat trials. The vertical line denotes the start of the torque pulse. The small inflections in the shoulder and elbow velocities at the beginning and end of the torque pulse largely reflect movement between the monkey's arm and the mechanical device due to compression of the soft tissue of the arm. Both the magnitude and time period for the applied loads can be controlled to monitor either small transient or longer sustained perturbations. Note that loads applied at either the shoulder or elbow joints will generate motion at both joints due to intersegmental interactions.

EXAMPLE 2

This example demonstrates that an instrument according to the invention can be used to identify impaired limb control resulting from brain dysfunction from such as stroke or trauma. A monkey was used as the subject, and brain activity in a region of the motor cortex was reversibly (ie., transiently) inhibited by injecting muscimol (1 $\mu$g in 1 $\mu$l saline; Sigma) into a small region of the monkey's primary motor cortex (see, for example, Martin, 1991; Martin et al. 1993). Muscimol is a GABA agonist which temporarily inhibits neural activity, resulting in reversible (i.e., transient) brain dysfunction. Muscimol injection was therefore used as a model to simulate brain dysfunction.

Figure 10:
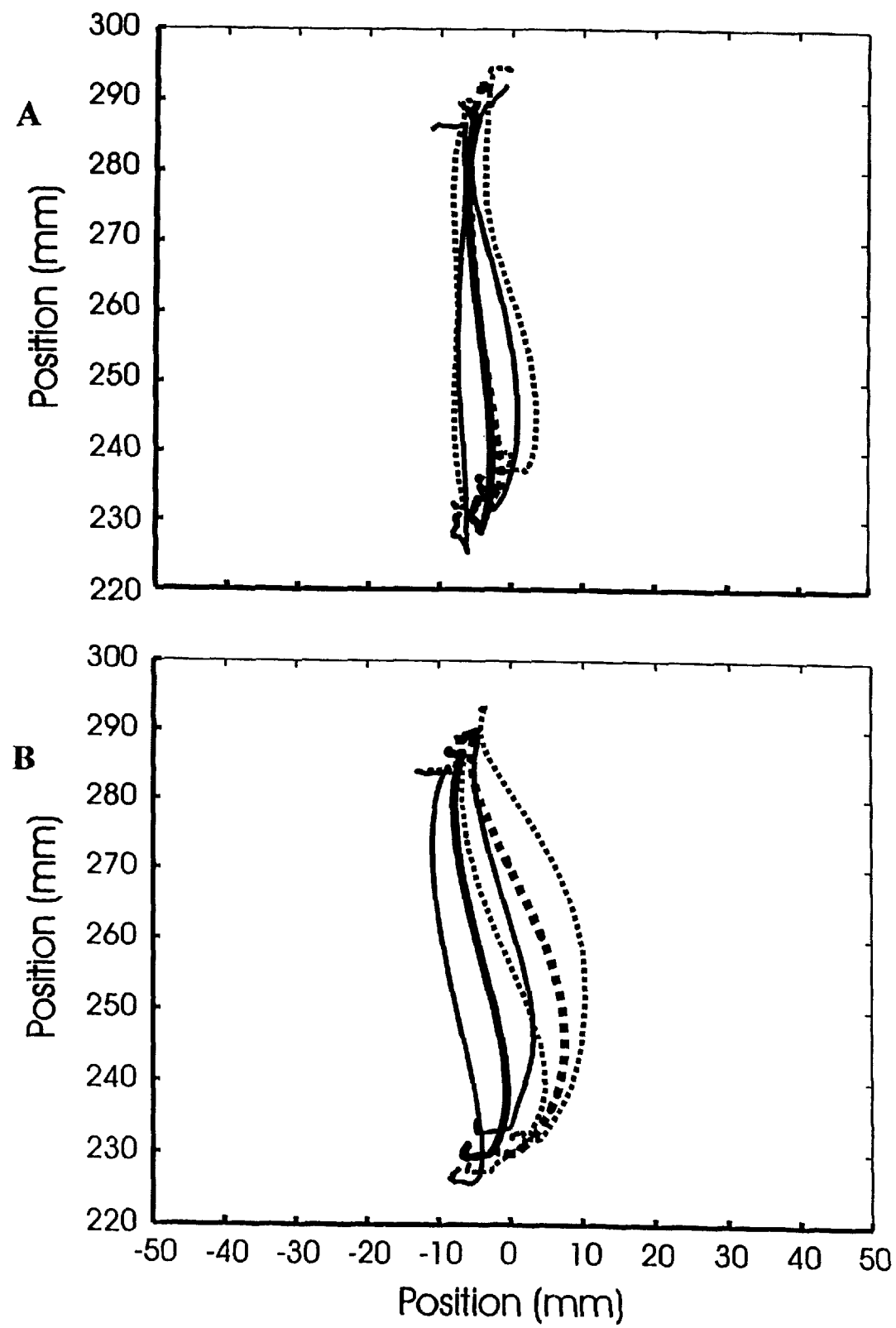
FIGS. 10A and 10B show hand trajectories of a monkey performing reaching movements using the embodiment of FIG. 1, without (A) and with (B) a viscous load applied to the elbow. These figures show that relative to the normal state (solid lines), inactivation of a small region of the motor cortex (dotted lines) was only evident when the subject was required to perform reaching movements with a viscous load applied to the elbow.

Hand trajectory of the monkey performing reaching tasks with and without viscous loads applied to the elbow joint, pre- and post-injection, are shown in FIG. 10. In the figure, pre-injection hand trajectories are shown as solid black lines, and post-injection hand trajectories are shown in dotted lines, with thick and thin lines represent the mean and standard deviation, respectively (six repeat trials). As can be seen from the figure, the injection of muscimol produced no observable change in motor function when reaching movements were performed without mechanical loads (FIG. 10A). In contrast, post-injection movements performed with viscous loads at the elbow joint are more curved relative to pre-injection movements (FIG. 10B). These results illustrate that a change in brain function (inactivation of a region of motor cortex) was only evident through the use of complex loads applied by the inventive instrument to the subject's elbow.

The invention has thus far been particularly shown and described with references to the preferred embodiment thereof, namely a kinesiological instrument comprising a four-bar linkage, Use of a four bar linkage in accordance with the invention allows the use of relatively heavy motors, such as torque motors, to load specific joints of a limb, because the motors are mounted on a separate housing rather than on the linkage itself. This provides the benefit of reducing the inertia of the linkage which, ideally, would be inertia-free. Additional benefits of the four-bar linkage and torque motors of the preferred embodiment include the ability to apply complex loads to one or more joints of a limb. Complex loads may include, for example, applying a torque at one joint that is proportional to the velocity of the other joint.

Torque motors are preferred because of the range of types of loads that they can apply to the joints of limbs. For example, the torque motors can apply viscous loads, as discussed in Example 1, static loads wherein the force is constant irrespective of the position of the joint, and perturbations wherein a force is applied as a pulse to one or more joints of the limb during movement. These types of loads are associated with various paradigms for investigating kinetics and kinematics of limb movement, as are well-known in the art. Any other type of suitable motor may also be employed in accordance with the invention, although other motors may not provide the range of loads that can be achieved with torque motors. The torque motors described above are also preferred because they have built-in encoders for providing angular position information Where other motors not having such encoders are employed, goniometers or similar measurement devices may be attached to joints of the linkage corresponding to joints of the limb under investigation, and electrically connected to a computer, to provide angular position information and feedback.

It should be understood that the invention is not limited to linkages employing torque motors and the like for applying forces to joints of limbs. Other devices can also be used to apply forces to limb joints, or resist movement of limbs. Such other devices include, for example, springs having dampers either integrally or associated therewith, or various hydraulic or pneumatic devices. Incorporation of other such other devices will of course limit the types of loads that can be applied to the joints of limbs, and hence limit the extensiveness of the types of data that can be obtained. Depending on the type of alternative device to be used, it may be necessary to employ devices such as goniometers as described above at the joints of the linkage if angular position data is to be obtained.

It should also be understood that the invention is not limited to linkages comprising four links. In a simpler form, a linkage in accordance with the invention can comprise only two links, such as links 402a and 416a in the case of the preferred embodiment (FIG. 2). Such a two-bar linkage could employ a single motor such as a torque motor mounted on a housing such as the housing 300 of the preferred embodiment. This, in combination with a goniometers disposed on the joint between the two links (i.e., at joint 408 in FIG. 2), would provide loading of the shoulder joint and joint angular position of both the shoulder and elbow joints, of an arm performing multi-joint reaching tasks, for example. Of course, loading devices other than motors, as discussed above, can also be disposed on a two-bar linkage in accordance with the invention. In particular, alternative loading devices that are compact and light-weight can be disposed on either or both of the joints of a two-bar linkage. A two-bar linkage having a joint loading device disposed at each of its two joints corresponding to, for example, the shoulder and elbow joints of an arm, would effectively provide for the same measures of kinetic and kinematic variables as the four-bar linkage of the invention.

In other embodiments of the invention, the linkage comprises three, five or another number of links. Moreover, the means providing a load need not be disposed on a stationary surface separate from the subject, but can be conveniently disposed on the trunk of the subject, or another stationary point.

It should also be understood that the invention is not limited to devices containing two or four-bar linkages so long as the same effect is achieved by another linkage. For example, in an alternative embodiment of the invention, arguably a simpler form, independent devices to monitor and modify mechanical loads are respectively and separately attached to each joint, the devices being linked to each other by appropriate circuitry. Each device spans a single joint and is firmly attached to the adjacent limb segments. In the case of the arm, one device spans the shoulder and one device spans the elbow. (That is, in the case of the shoulder joint, the device may be attached to the subject's upper arm and trunk, with the joint therebetween.) Each device provides positional feedback and applies a load at its spanned joint. In effect, the upper arm of the subject provides the rigid link between the device acting at the shoulder with the device acting at the elbow.

Yet other changes may be made to the preferred embodiment without departing from the scope of the invention. For example, in the preferred embodiment, the axes of rotation of the joints on the instrument are aligned substantially in the vertical direction so that limb motion occurs in and is restricted to the horizontal plane. Through simple changes in the design, the instrument can be re-oriented to allow for movement in other planes, such as the vertical plane. Such changes in the design would permit the instrument to be used for investigating leg movement, for example. In investigations involving the leg, movement of the hip and knee joints, for example, would be of interest.

REFERENCES

Caminiti R, Johnson P B, Burnod Y, Galli C, and Ferraina S. Shift of preferred directions of promotor cortical cells with arm movements performed across the workspace. Exp Brain Res 1990a;83:228–32.

Caminiti R, Johnson P B, and Urbano A. Making arm movements within different parts of space: dynamic aspects in the primate motor cortex. J Neurosci 1990b;10:2039–58.

Cisek P, Scott S H. Cooperative action for mono- and bi-articular arm muscles during multi-joint posture and movement tasks in monkeys. Society for Neuroscience Abstracts 1998;

Georgopoulos A P. Current issues in directional motor control. [review]. Trends Neurosci 1995;18:506–10.

Gomi H and Kawato M. Equilibrium-point control hypothesis examined by measured arm stiffness during multijoint movement. Science 1996;272:117–20.

Goodbody S J and Wolpert D M. Temporal and amplitude generalization in motor learning. J Neurophysiol 1998;79:1825–38.

Hollerbach J M and Flash T. Dynamic interactions between limb segments during planar arm movement. Biol Cybern 1982;44:67–77.

Kalaska J F, Cohen D A, Hyde M L, and Prud'homme M. A comparison of movement direction-related versus load direction-related activity in primate motor cortex, using a two-dimensional reaching task. J Neurosci 1989;9:2080–102.

Kalaska J F and Crammond D J. Cerebral cortical mechanisms of reaching movements. [review]. Science 1992;255:1517–23.

Karst G M and Hasan Z. Timing and magnitude of electromyographic activity for two-joint arm movements in different directions. J Neurophysiol 1991;66:1594–604.

Lackner J R and DiZio P. Rapid adaptation to coriolis force perturbations of arm trajectory. J Neurophysiol 1994;72:299–313.

Martin J H. Autoradiographic estimation of the extent of reversible inactivation produced by microinjection of lidocaine and muscimol in the rat. Neurosci Lett 1991;127:160–164.

Martin J H, Ghez C. Differential impairments in reaching and grasping produced by local inactivation within the forelimb representation of the motor cortex in the cat. Exp Brain Res 1993; 94:429–443.

O'Sullivan S B, Schmitz T J. Physical Rehabilitation: Assessment and Treatment. 3rd. Philadelphia: F.A. Davis Co. 1994;

Scott S H and Kalaska J F. Reaching movements with similar hand paths but different arm orientations: I. Activity of individual cells in motor cortex. J Neurophysiol 1997;77:826–52.

Shadmehr R and Mussa-Ivaldi F A. Adaptive representation of dynamics during learning of a motor task. J Neurosci 1994;14:3208–24.

Shen L and Alexander G E. Neural correlates of a spatial sensory-to-motor transformation in primary motor cortex. J Neurophysiol 1997;77:1171–94.

Soechting J F and Flanders M. Moving in three-dimensional space: frames of reference, vectors, and coordinate systems. Ann Rev Neurosci 1992; 15:167–91.

Turner R S, Owens J W, Jr., and Anderson M E. Directional variation of spatial and temporal characteristics of limb movements made by monkeys in a two-dimensional work space. J Neurophysiol 1995;74:684–97.

Van Deusen J, Brunt D. Assessment in Occupational Therapy and Physical Therapy. Philadelphia: W.B. Saunders Co. 1997;

Winter D A. Biomechanics and Motor Control of Human Movement. 2nd. New York: John Wiley & Sons, Inc. 1990;

Zajac F E, Gordon M E. Determining muscle's force and action in multi-articular movement. In: Pandolf K B, editors. Exercise and sport sciences reviews. Williams & Wilkins, Baltimore: 1989;187–230.

I claim:

1. An instrument for monitoring the kinesiology of multi-joint limb motion, comprising:
    a linkage having four links connected at four joints, each joint having articulation about an axis, the four axes of articulation being substantially parallel;
    limb coupling means for coupling a limb to said linkage, the limb coupling means maintaining alignment of centers of rotation of two joints of the limb with centers of rotation of two joints of the linkage;
    means for providing a load to at least one of said two joints of the linkage; and
    means for obtaining data respecting angular position of at least one of said joints of said linkage.

2. An instrument according to claim 1, wherein said linkage having four articulating joints is in the configuration of a parallelogram.

3. An instrument according to claim 1, wherein the load is provided by a motor.

4. An instrument according to claim 3, wherein the motor is a torque motor.

5. An instrument according to claim 4, wherein two torque motors are employed, one for providing a load to each of said joints of the linkage aligned with joints of the limb.

6. An instrument according to claim 1, wherein said load is selected from the group consisting of viscous loads, static loads, and perturbations.

7. An instrument according to claim 2, wherein one of said links of the linkage has a portion which extends substantially beyond the parallelogram.

8. An instrument according to claim 7, wherein the limb is an arm, and wherein two limb coupling means are disposed on the linkage, one on the extended link portion for coupling to the forearm, and another on an adjacent link for coupling to the upper arm, such that the centers of rotation of the shoulder joint and elbow joint are maintained in alignment with centers of rotation of two joints of the linkage.

9. An instrument according to claim 1, further comprising torque sensors for obtaining data relating to the torque applied to the linkage by the load.

10. An instrument according to claim 1, further comprising an accelerometer for obtaining data relating to the acceleration of at least a portion of the linkage when moved by a limb.

11. An instrument according to claim 7, further comprising an accelerometer for obtaining data relating to the acceleration of at least a portion of the linkage when moved by a limb, wherein the accelerometer is disposed on a distal end of the extended link portion of the linkage.

12. An instrument for monitoring the kinesiology of multi-joint limb motion, comprising:
    a linkage having two links connected at a joint having articulation about a first axis;
    a second axis defined at a point near the terminus of one of said links, the second axis being substantially parallel to the first axis;
    limb coupling means for coupling a limb to said linkage, the limb coupling means maintaining alignment of centers of rotation of two joints of the limb with centers of rotation of the first and second axes;
    means for providing a load to at least one of said axes; and
    means for obtaining data respecting angular position of at least one of said axes.

13. An instrument according to claim 12, wherein the load is provided to said second axis.

14. An instrument according to claim 12, wherein the load is provided by a torque motor.

15. An instrument according to claim 12, wherein said load is selected from the group consisting of viscous loads, static loads, and perturbations.

16. An instrument according to claim 12, wherein the limb is an arm, and wherein a coupling means is disposed on each link of the linkage for coupling the forearm to one link and the upper arm to the other link, such that the centers of rotation of the shoulder joint and elbow joint are maintained in alignment with centers of rotation of the two axes of the linkage.

17. An instrument according to claim 12, further comprising a torque sensor for obtaining data relating to the torque applied to at least a portion of the linkage by the load.

18. An instrument according to claim 12, further comprising an accelerometer for obtaining data relating to the acceleration of at least a portion of the linkage when moved by a limb.

19. An instrument according to claim 18, wherein an accelerometer is disposed on a distal portion of the linkage.

20. A method for detecting a neural and/or muscular problem associated with impaired movement of a limb, comprising:
    providing a linkage having four links connected at four joints, each joint having articulation about an axis, the four axes of articulation being substantially parallel;
    coupling a limb to said linkage, wherein centers of rotation of two joints of the limb are aligned with centers of rotation of two joints of the linkage;
    providing a load to at least one of said two joints of the linkage; and
    obtaining data respecting angular position of at least one of said joints of said linkage;
    wherein the data respecting angular position is indicative of a neural and/or muscular problem associated with impaired movement of a limb.

21. A method according to claim 20, wherein said linkage having four articulating joints is in the configuration of a parallelogram.

22. A method according to claim 20, wherein the load is applied to each of said joints of the linkage aligned with joints of the limb.

23. A method according to claim 22, wherein the load is applied independently to each of said joints by a motor associated with each joint.

24. A method according to claim 23, wherein the motors are torque motors.

25. A method according to claim 24, wherein the load is provided in a form selected from the group consisting of viscous loads, static loads, and perturbations.

26. A method according to claim 21, wherein one of said links of the linkage has a portion which extends substantially beyond the parallelogram.

27. A method according to claim 21, wherein the limb is an arm, and wherein the coupling of the arm to the linkage maintains the centers of rotation of the shoulder joint and elbow joints in alignment with centers of rotation of two joints of the linkage.

28. A method according to claim 20, further comprising obtaining data respecting torque applied to at least a portion of the linkage as a result of a load being applied;
    wherein the data respecting torque is indicative of a neural and/or muscular problem associated with impaired movement of a limb.

29. A method according to claim 20, further comprising obtaining data respecting acceleration of at least a portion of the linkage when moved by a limb;
    wherein the data respecting acceleration is indicative of a neural and/or muscular problem associated with impaired movement of a limb.

30. A method for monitoring a neural and/or muscular problem associated with impaired movement of a limb, comprising:
    providing a linkage having four links connected at four joints, each joint having articulation about an axis, the four axes of articulation being substantially parallel;
    coupling a limb to said linkage, wherein centers of rotation of two joints of the limb are aligned with centers of rotation of two joints of the linkage;
    providing a load to at least one of said two joints of the linkage; and
    obtaining data respecting angular position of at least one of said joints of said linkage;
    wherein the data respecting angular position is related to status of the neural and/or muscular problem associated with impaired movement of a limb.

31. A method for treating a neural and/or muscular problem associated with impaired movement of a limb, comprising:
    providing a linkage having four links connected at four joints, each joint having articulation about an axis, the four axes of articulation being substantially parallel;
    coupling a limb to said linkage, wherein centers of rotation of two joints of the limb are aligned with centers of rotation of two joints of the linkage;
    providing a load to at least one of said two joints of the linkage; and
    obtaining data respecting angular position of at least one of said joints of said linkage;
    wherein the data respecting angular position is related to progress of the neural and/or muscular problem associated with impaired movement of a limb.

32. A method for detecting a neural and/or muscular problem associated with impaired movement of a limb, comprising:
    providing a linkage having two links connected at a joint having articulation about a first axis;
    defining a second axis at a point near the terminus of one of said links, the second axis being substantially parallel to the first axis;
    coupling a limb to said linkage such that centers of rotation of two joints of the limb are maintained in alignment with centers of rotation of the first and second axes; and
    providing a load to at least one of said axes; and
    obtaining data respecting angular position of at least one of said axes;
    wherein the data respecting angular position is indicative of a neural and/or muscular problem associated with impaired movement of a limb.

33. A method according to claim 32, wherein the load is provided to said second axis.

34. A method according to claim 32, wherein the load is provided by a torque motor.

35. A method according to claim 34, wherein said load is selected from the group consisting of viscous loads, static loads, and perturbations.

36. A method according to claim 32, wherein the limb is an arm, and wherein the coupling of the arm to the linkage maintains the centers of rotation of the shoulder joint and elbow joints in alignment with centers of rotation of the two axes of the linkage.

37. A method according to claim 32, further comprising obtaining data respecting torque applied to at least a portion of the linkage as a result of a load being applied;

wherein the data respecting torque is indicative of a neural and/or muscular problem associated with impaired movement of a limb.

38. A method according to claim 32, further comprising obtaining data respecting acceleration of at least a portion of the linkage when moved by a limb;

wherein the data respecting acceleration is indicative of a neural and/or muscular problem associated with impaired movement of a limb.

39. A method for monitoring a neural and/or muscular problem associated with impaired movement of a limb, comprising:

providing a linkage having two links connected at a joint having articulation about a first axis;

defining a second axis at a point near the terminus of one of said links, the second axis being substantially parallel to the first axis;

coupling a limb to said linkage such that centers of rotation of two joints of the limb are maintained in alignment wit centers of rotation of the first and second axes; and providing a load to at least one of said axes; and obtaining data respecting angular position of at least one of said axes;

wherein the data respecting angular position is indicative of status of the neural and/or muscular problem associated with impaired movement of a limb.

40. A method for treating a neural and/or muscular problem associated with impaired movement of a limb, comprising:

providing a linkage having two links connected at a joint having articulation about a first axis;

defining a second axis at a point near the terminus of one of said links, the second axis being substantially parallel to the first axis;

coupling a limb to said linkage such that centers of rotation of two joints of the limb are maintained in alignment with centers of rotation of the first and second axes;

providing a load to at least one of said axes; and obtaining data respecting angular position of at least one of said axes;

wherein the data respecting angular position is indicative of progress of the neural and/or muscular problem associated with impaired movement of a limb.

* * * * *